(12) United States Patent
Schlegel et al.

(10) Patent No.: US 7,039,448 B2
(45) Date of Patent: May 2, 2006

(54) ZERO CORRECTED OPTICAL BLOOD ANALYTE DETECTOR

(75) Inventors: Robert P. Schlegel, Carroll, OH (US); John M. Rihl, Fort Pierre, SD (US); Steven V. Ricca, Upper Arlington, OH (US)

(73) Assignee: DIRAmed, LLC, Carroll, OH (US)

( * ) Notice: Subject to any disclaimer, the term of this patent is extended or adjusted under 35 U.S.C. 154(b) by 221 days.

(21) Appl. No.: 10/832,873

(22) Filed: Apr. 27, 2004

(65) Prior Publication Data

US 2004/0220459 A1 Nov. 4, 2004

Related U.S. Application Data

(60) Provisional application No. 60/467,344, filed on May 2, 2003.

(51) Int. Cl.
*A61B 5/00* (2006.01)
(52) U.S. Cl. .................. 600/316; 600/310; 600/473
(58) Field of Classification Search ............... 600/310, 600/316, 322, 473
See application file for complete search history.

(56) References Cited

U.S. PATENT DOCUMENTS

| 6,990,364 B1* | 1/2006 | Ruchti et al. ............... 600/310 |
| 2003/0050541 A1* | 3/2003 | Wuori ........................ 600/316 |
| 2005/0106651 A1* | 5/2005 | Chaiken et al. ............... 435/14 |

* cited by examiner

*Primary Examiner*—Eric F. Winakur
*Assistant Examiner*—Vivek Natarajan
(74) *Attorney, Agent, or Firm*—Mueller and Smith,LPA (57) ABSTRACT

The present invention is directed to method and apparatus for non-invasively measuring the concentration of an unknown blood analyte present in a patient. The method involves determining the concentration of a reference analyte present in the patient. Using the non-invasive optical instrument of the invention, the concentrations of the reference analyte and unknown analyte are measured. If the measured reference analyte concentration and determined reference analyte concentration are substantially the same, then the measured unknown analyte concentration is displayed. If the measured reference analyte concentration and determined reference analyte concentration are not substantially the same, then an adjustment factor is applied to the measured unknown analyte concentration and the unknown analyte concentration is displayed.

17 Claims, 12 Drawing Sheets

ZERO CORRECTED OPTICAL BLOOD ANALYTE DETECTOR

CROSS-REFERENCE TO RELATED APPLICATIONS

This application claims the benefit of U.S. Provisional Application Ser. No. 60/467,344, filed May 2, 2003, the disclosure of which is hereby incorporated by reference.

STATEMENT REGARDING FEDERALLY SPONSORED RESEARCH

Not applicable.

BACKGROUND OF THE INVENTION

Diabetes Mellitus is one of the most common chronic diseases in the United States. A disease without a cure, it is estimated that 15,000,000 United States adults (about 7.2% of the total adult population) have diagnosed diabetes. In 1997, an international committee sponsored by the American Diabetes Association (ADA) recommended changes to the two diabetes classifications such that they are now referred to as Types 1 and 2. Type 1 is referred to as an insulin dependent diabetes mellitus. Type 2, or non-insulin dependent diabetes ellitus, occurs in 90–95% of the diabetic population.

Monitoring glycemic status is paramount in the treatment of diabetes because it provides the means to evaluate the efficacy of treatment and guide further therapeutic interventions. Such monitoring traditionally has been achieved by a combination of testing during office visits and self-monitoring of blood glucose (SMBG) by patients on a daily basis. The most common SMBG method has been the use of capillary blood glucose monitors; however, newer glucose monitoring technologies are emerging.

In general, there are barriers to self-monitoring of blood glucose. These have been identified as:
  (a) inadequate understanding by patients;
  (b) inadequate understanding by health care providers;
  (c) inconvenience;
  (d) psychosocial discomfort;
  (e) physical discomfort;
  (f) expense; and
  (g) complexity of device Attempts over the years have been made to develop a reasonably accurate non-invasive glucose measurement using optical techniques and the like. However, these devices have exhibited excessive inaccuracies. See generally Waynant,et al., "Overview of Non-invasive Fluid Glucose Measurement Using Optical Techniques to Maintain Glucose Control In Diabetes Mellitus," which is incorporated herein by reference.

Optical techniques additionally are described in U.S. Pat. No. 5,313,941 by Braig, et al., entitled "Non-Invasive Pulsed Infrared Spectrophotometer," which additionally is incorporated herein by reference.

SUMMARY OF THE INVENTION

The present invention is directed to method and apparatus for non-invasively measuring the concentration of an unknown blood analyte, such as glucose. The method involves utilizing conventional analysis to determine the concentration of a reference analyte, such as cholesterol, which does not significantly change over time. Then, using the non-invasive optical instrument of the invention, the concentrations of the reference analyte and unknown analyte are measured. If the measured reference analyte concentration and determined reference analyte concentration are substantially the same, then the measured unknown analyte concentration is displayed. If the measured reference analyte concentration and determined reference analyte concentration are not substantially the same, then an adjustment factor is applied to the measured unknown analyte concentration and the unknown analyte concentration is displayed.

The non-invasive optical instrument of the invention includes an IR source with an output which will extend through a target such as a finger or the web of the hand or the like to then be detected by an IR optical detector. The output correlates with the reference analyte concentration and the unknown analyte concentration. A signal treatment system, which may be part of the optical detector, converts the R output into the reference analyte concentration and unknown analyte concentration. The signal treatment system also provides an important autozeroing of the optical detector. A microprocessor, with associated memory, is programmed to compare the predetermined reference value with that measured by the instrument. If the predetermined value and the measured values for the reference analyte are substantially the same, then the microprocessor transmits the measured value of the unknown analyte to a display. If the predetermined reference value and the measured reference value are not substantially the same, then the microprocessor applies an adjustment factor to the unknown analyte concentration. That adjusted concentration then is transmitted to the display. The adjustment factor may be selected from a look-up table of values based on the concentration difference between the predetermined reference analyte concentration and the measured reference concentration.

DETAILED DESCRIPTION OF THE INVENTION

The present invention is concerned with the monitoring of blood analytes and, in particular, is directed to accurate non-invasive spectrographic analysis measuring in vivo analytes and, in particular, glucose concentrations utilizing signal processing of near-infrared measurements. Such signal processing comprises an autozeroing of an infrared detector circuit and evaluating a first or reference blood analyte concentration which, for most humans shows very little variance over extended periods of time. For example, the reference analyte should change by no more than 20% within a 3 month time period. That means that at the end of a 3 month time frame, the reference value should be not be more than higher or lower than the initial value measured. In this regard, cholesterol levels basically are generated in the liver. For diabetic patients, typically food intake is carefully controlled as well as exercise regime. As a consequence, the cholesterol analyte represents an ideal reference. The patient initial cholesterol level is analyzed in conventional manner at the onset of utilizing the apparatus and method of the invention. This initial determination of the reference analyte concentration may be accomplished, for example, by conducting an in vitro blood sample analysis. The value for cholesterol is retained in memory and is employed to evolve a correction factor for an essentially simultaneous measurement using infrared based optics for glucose. Accordingly, none of the elaborate algorithms attempting to correct poor data are employed. While cholesterol is a particularly advantageous reference for diabetics, keratin is another example of a suitable reference analyte as its concentration does not change significantly over extended periods of time.

Preferably, the measurement of glucose and cholesterol will be simultaneous, but some temporal deviation is permissible. Blood flow and changes in blood flow affect the optical cholesterol and glucose measurements. Therefore, in order to assure that the blood flow or changes in blood flow do not affect the cholesterol and glucose signals differently, the two measurements should be taken essentially simultaneously so that the relative distortion of the signals is the same. Generally, the distortion of the signals should be different by no more than 10 percent. For example, the measurements should be taken within a smaller time interval than a human heartbeat frequency. This avoids pathlength differences caused by the blood pressure's temporary swelling of the target site on each heartbeat. Translating that into a physical example, for a heartbeat rate of 120 beats per minute, the measurements should be taken within 5 milliseconds of one another. That time would expand as the heart rate decreases and contract as the heart rate increases.

Figure 1:
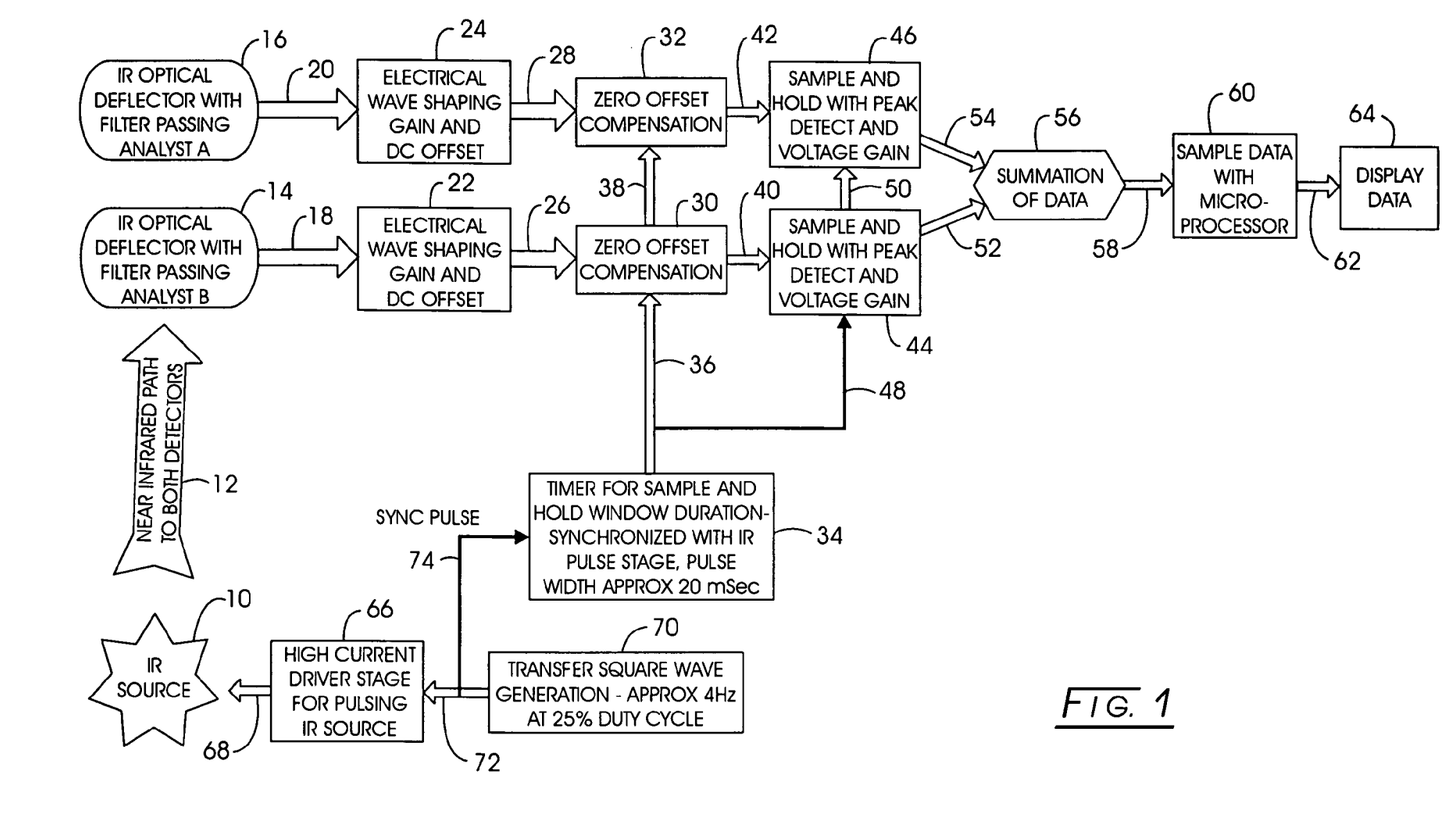
FIG. 1 is a block diagram of circuitry functions employed with the apparatus of the invention.

Looking to FIG. 1, a block diagram of the circuitry functions employed with the invention is set forth. In the figure, the IR source is shown at 10 generating an R output represented at arrow 12 which will extend or penetrate through a target such as a finger or the web of the hand or the like. The resulting tissue IR output then is detected by an IR optical detector with a filter passing an analyte B signal at 14 and an IR optic detector with a filter passing representations of an analyte A as represented at 16. In general, a single IR source is utilized in conjunction with two optical filters having different pass characteristics. As an example, analyte A may be cholesterol while analyte B may be glucose. Alternatively, analyte A may be keratin. The optodetectors will preferably be in very close proximity and may be incorporated within a singular component. Outputs of detectors 14 and 16 are represented at respective arrows 18 and 20. Each such output is directed to a signal treatment system with electrical wave shaping, gain, and DC offset functions represented respectively at blocks 22 and 24. These analog conditioning circuits are configured with the knowledge that there are certain levels of signal that maybe expected and which the circuit is poised to extract. However, while an AC output will be evolved due to a pulsing of IR source 10, there generally will be a DC term representing noise. Accordingly, as represented at arrows 26 and 28 the DC term is evaluated. That DC term then is disposed of as represented at respective blocks 30 and 32 providing for zero offset or autozeroing compensation under the synchronized control of a timer function represented at block 34, such synchronization input being represented at arrows 36 and 38.

Following the compensation represented at blocks 30 and 32, as represented at respective arrows 40 and 42, the AC signals are submitted to sample and hold circuits having peak detection and voltage gain functions. Those components are represented at respective blocks 44 and 46. Sample and hold synchronization is provided from timer function 34 as represented by arrows 48 and 50. The gain supplied at stages 44 and 46 is developed to provide an instrument gain with, for example, a range from zero to 10 volts or the like. The now conditioned signals for analytes B and A are submitted, as represented at respective arrows 52 and 54 to a summation function represented at block 56. This summation function may be carried out in a microprocessor. In this regard, after subtracting the DC levels from zero offset compensation, the amplitude value desired will be the amplitude value for analyte B minus the amplitude value of analyte A. That value, for example, is submitted as represented at arrow 58 to digitization and conversion to a corrected value for analyte B, for example, glucose. A microprocessor function, and associated memory for storing values such as the determined reference concentration, optically measured concentrations, and the like, is represented at block 60. The resultant numeric value then may be displayed as represented at arrow 62 and block 64.

Returning to the IR source 10, source 10 is driven by a high current driver stage as represented at block 66 and arrow 68. Drive 66, in turn, is pulsed from a squarewave generator as shown at block 70 and represented by arrow 72. Synchronization from the timer 70 also is provided to timer 34 as represented by arrow 74.

Microprocessor function 60 serves to compare the reference analyte value with the pre-tested analyte values, such as that for cholesterol. If the measured reference analyte value is substantially the same as the pre-tested analyte value, then the measured value of analyte A, i.e., glucose, will be displayed. However, if the measured and pre-determined values for the reference concentration are not the same, an adjustment factor then will be computed and applied to the value of the analyte. Then, through simple table lookup procedures, the processor will publish a numeric value for analyte A, for example, glucose. An adjustment factor may be applied for any difference noted between the determined and measured reference values; however, the difference generally will be significant and an adjustment desired if the two values vary by 0.5 percent or more.

Figure 2:
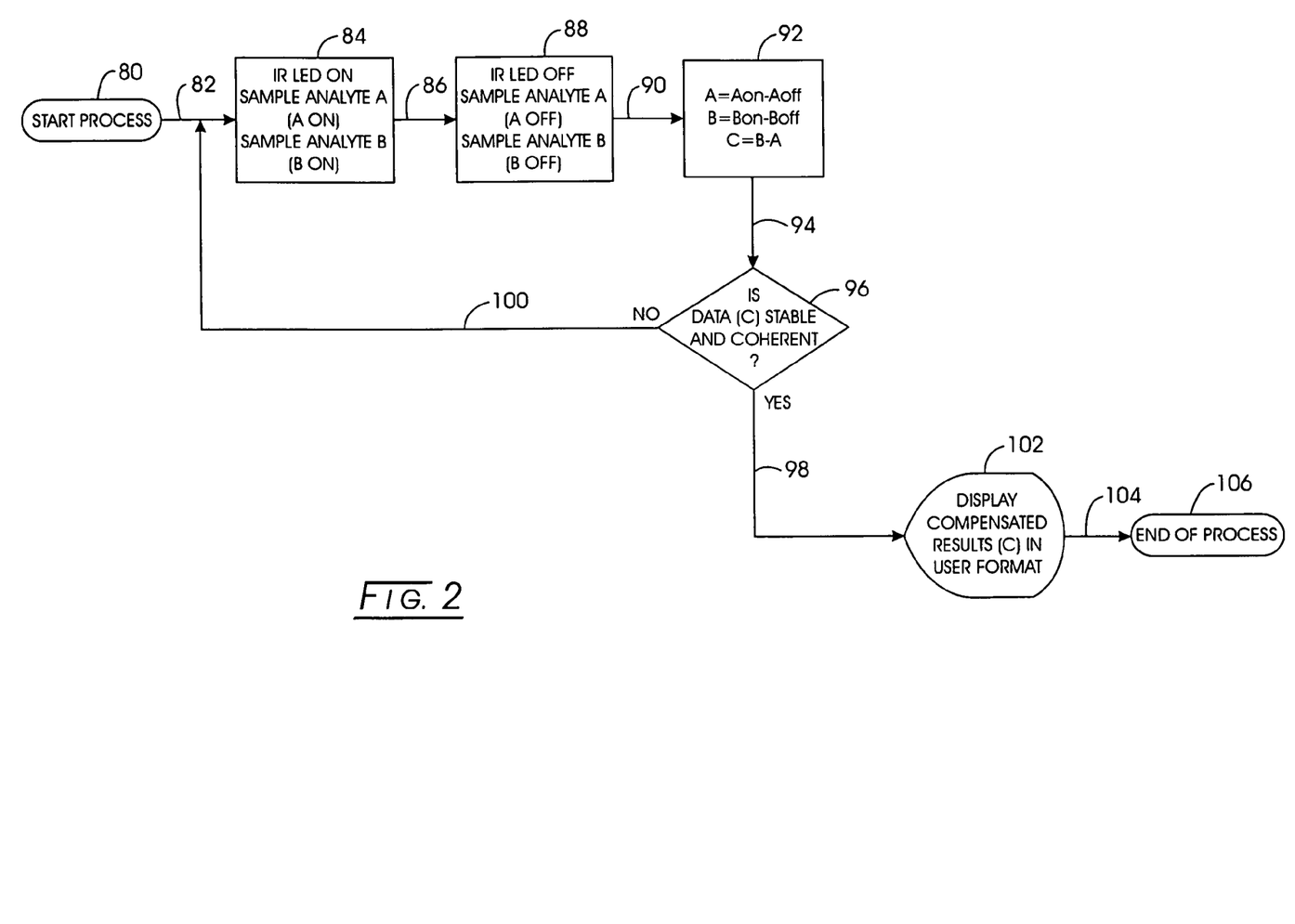
FIG. 2 is a block diagram showing a typical operational sequence of apparatus according to the invention.

Referring to FIG. 2, an operational sequence for the inventive approach is set forth. The process is seen to commence at node 80 and arrow 82 extending to block 84.

Block 84 provides for turning the infrared LED on and carrying out the sampling of analyte A (Aon) and analyte B (Bon). Then, as represented at arrow 86 and block 88 the IR source is turned off and again analyte A is sampled (Aoff) as well as analyte B (Boff). This provides the information for accommodating the DC noise term. Then, as represented at arrow 90 and block 92 the value and amplitude for analyte A is set to Aon–Aoff; the value of analyte B is Bon–Boff. Next, the value for the measured, as opposed to reference analyte, is simply the value for analyte B less the value for analyte A. Then, as represented at arrow 94 and block 96 a sequence of C values are evaluated for stability and coherence. For example, if the rapidly occurring values for C are essentially the same, then valid data is present and the program logic continues as represented at arrow 98. If such stability and coherence are not present, then as represented at arrow 100, the program will revert to arrow 82 to start the process again.

Arrow 98 is seen to extend to symbol 102 providing for the display of compensated results in user readable format. Then, as represented at arrow 104 and node 106 the process is ended.

Figure 3:
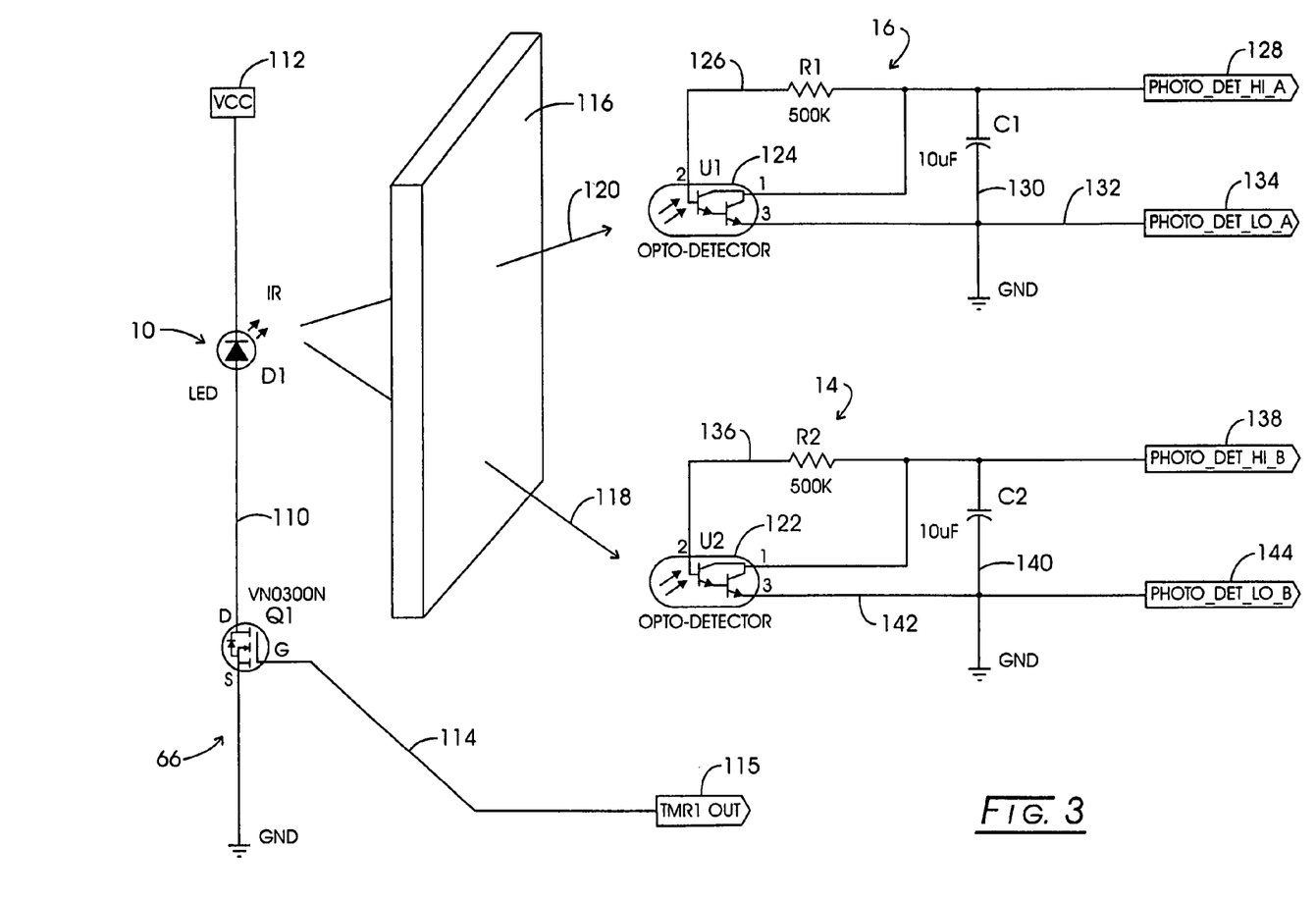
FIG. 3 is a schematic diagram showing an infrared emitter and opto-detectors for two channels.

Referring to FIG. 3, the near infrared emitter and optodetector features are revealed. IR source 10 is here seen as a light emitting diode (LED) D1 coupled within line 110 between VCC 112 and ground (GND). Interposed between ground and diode D1 is a field effect transistor Q1, the source and drain terminals of which are coupled respectively between ground and diode D1. The gate of transistor Q1 is coupled as represented at line 114 to a timer 1 out flag 115.

When emitting, the output of diode D1 is directed through a target sample symbolically represented at 116 in conjunction with light pencils 118 and 120. Light pencil 118 is shown directed to opto-detector 122 while analyte A light pencil 120 is shown directed to opto-detector 124. One component of the resultant output of device 124 is directed via line 126 to provide a photo detector HI signal as represented at flag 128. Line 126 additionally is seen filtered by a capacitor C1 extending within line 130 between line 126 and ground. A line 127 incorporating resistor R1 extends from device 124 to line 126. The second output component of the device is presented along line 132 and is identified at flag 134 as photo detector LO.

In identical fashion, opto-detector 122 provides one output component at line 136. This derives a photo detector HI output for analyte B as represented at flag 138. Line 136 is shown filtered by a capacitor C2 within line 140 extending between line 136 and ground. A line 137 incorporating resistor R1 extends from device 122 to line 136. The second component of the output of device 122 is represented at line 142 extending to provide a photo detector low output as represented at flag 144.

Figure 4:
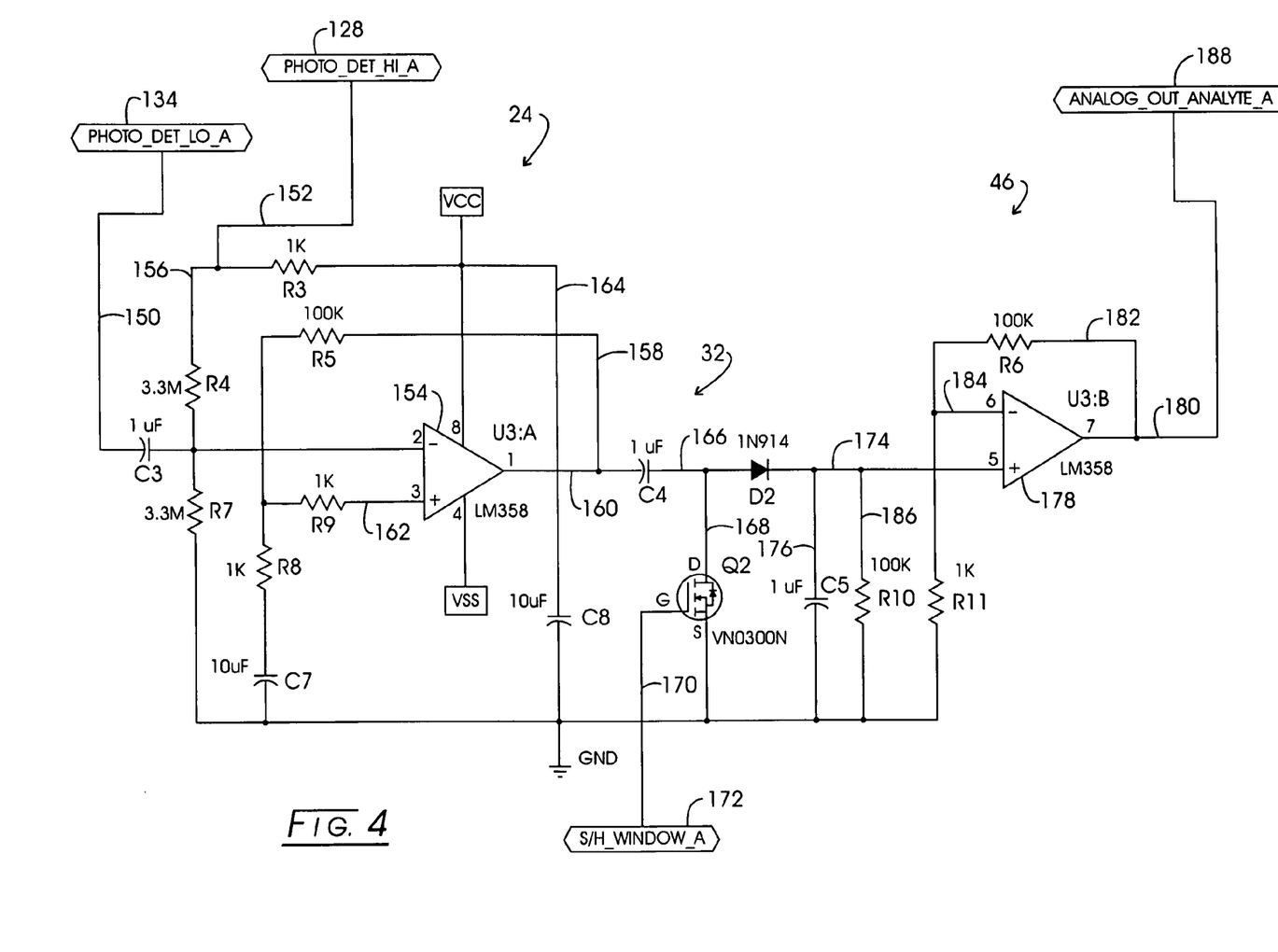
FIG. 4 is an electrical schematic diagram showing circuitry for analog conditioning and sampling of analyte A.

Referring to FIG. 4, the analog conditioning and sampling circuitry for treating analyte A is revealed. In FIG. 4, the output of opto-detector 124 for analog A is shown again with flags 128 and 134. Output component 134, carrying the photo detect LO A output component, is seen sending the component to conditioning circuitry via line 150, while the corresponding output represented at flag 128 for photo detect HI A is seen being directed to that circuit via line 152. Line 150 is directed through a coupling capacitor C3 to the inverting input of an operational amplifier 154. Line 152, carrying the opposite input component, is directed to line 156 incorporating divider resistors R4 and R7. Those resistors adjust the DC offset value to about half of the positive voltage.

The opposite input to operational amplifier 154 is provided from line 158 extending from output line 160 and incorporating resistors R5, R8 and capacitor C7. These components in combination with resistor R9 at line 162 extending to the device 154 non-inverted input establish a more useful range of signals. Resistor R3 within line 156 is seen to extend from supply VCC. That line also is filtered as represented at line 164 and capacitor C6.

Output line 160 is seen directed to capacitor C4 which functions as an AC coupler and also a DC term block. The opposite side of capacitor C4 is coupled via line 166 to the anode of diode D2. However, note that an FET Q2 may be turned on to draw line 166 to ground via line 168. In this regard, FET Q2 is turned on from gate line 170, line 170 being controlled from a sample and hold window A signal represented at flag 172. Diode D2 performs as a steering device carrying out an absolute value function and serves to trap the signal passing therethrough at line 174. A signal at line 174 having passed diode D2 will charge capacitor C5 within line 176. That sampled peak voltage from capacitor C5 is directed via line 174 to the non-inverting input of operational amplifier 178. Amplifier 178 additionally is configured such that its output at line 180 is coupled via line 182 incorporating resistor R6 to its inverting input via line 184. That network also includes resistor R11. A resistor R10 is seen to be located within line 186 extending between line 174 and ground. With the arrangement shown, working instrument gain voltage levels are developed and the output of device 178 at line 180 is the analog output DC value for analyte A. That output is represented at flag 188.

Figure 5:
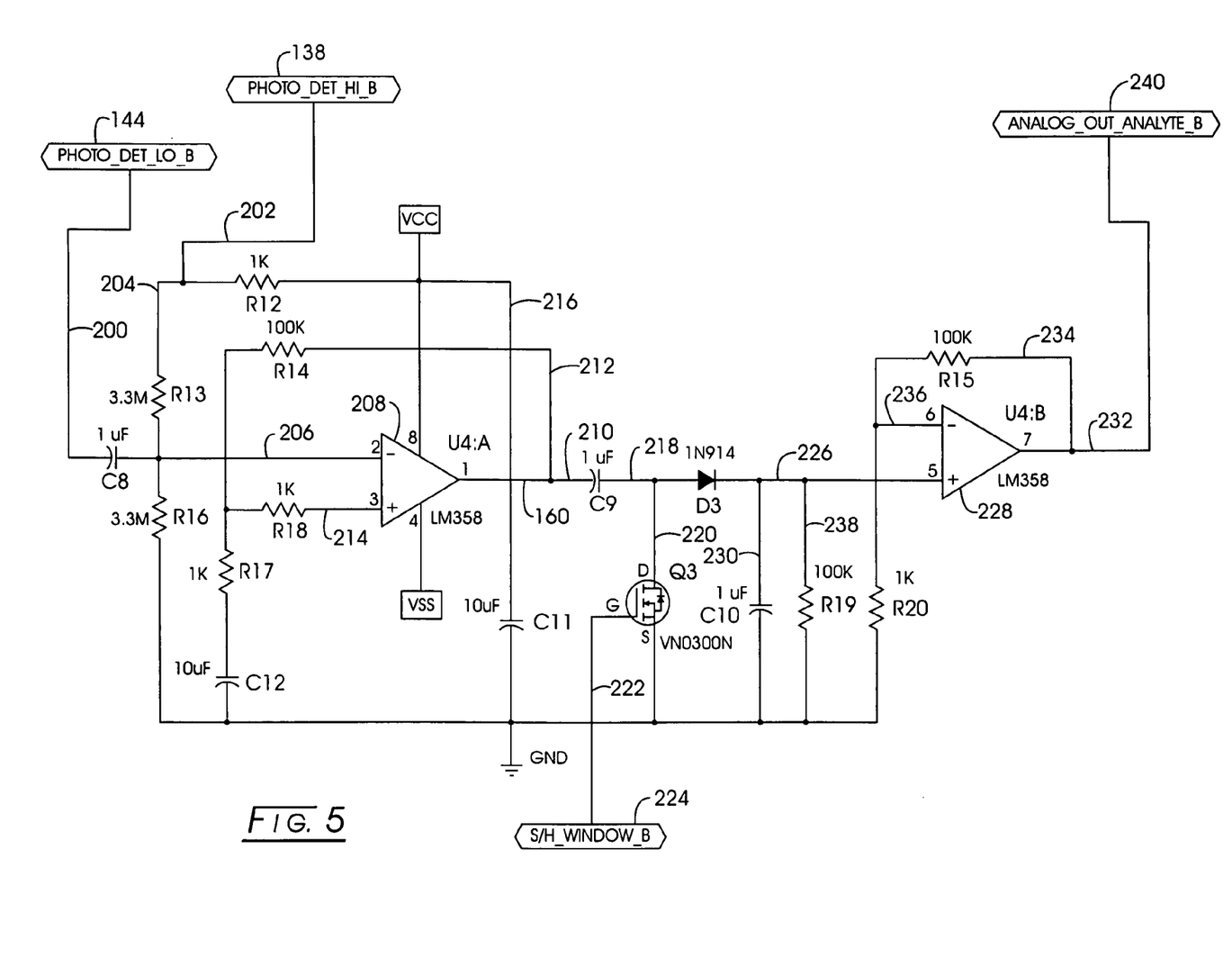
FIG. 5 is an electrical schematic diagram showing circuitry for analog conditioning and sampling of analyte B.

FIG. 5 presents an identical circuit configured for the treatment of the combined outputs of opto-detector 122. Accordingly, flags 138 and 144 reappear from FIG. 3, the photo detect LO B signal as represented at flag 144 being introduced via line 200 to coupling capacitor C8. Correspondingly, the photo detect HI B output component represented at flag 138 is seen directed via lines 202 and 204 to line 206 positioned on the opposite side of capacitor C8 and directed, in turn, to the inverting output of operational amplifier 208. Line 204 incorporates divider resistors R13 and R16 as well as resistor R12 extending to supply VCC. Bias to device 208 is derived from output line 210, line 212 and input line 214 extending to its non-inverting input of device 208. Bias is developed with respect to device 208 by resistors R14, R17 and R18 along with capacitor C12. A filter capacitor C11 is coupled at line 216 between VCC and ground.

Output line 210 is directed to coupling capacitor C9 which functions to strip the DC term from it and provide an AC signal at line 218. Line 218 extends to the anode of steering and absolute value functioning diode D3. A field effect transistor Q3 is seen coupled within line 220 extending between line 218 and ground and is turned on from a gate input line 222 which carries the sample and hold window B input represented at flag 224. The opposite side of diode D3 is coupled with line 226. When transistor Q3 is off or open circuited, diode D3 transmits the signal from line 218 to charge sampling capacitor C10 to some peak value. That value is asserted via line 226 to the non-inverting input of operational amplifier 228. Capacitor C10 is seen to be positioned within line 230 extending between line 226 and ground. The output at line 232 of amplifier 228 is coupled via lines 234 and 236 to its inverting input. Line 234 is seen to incorporate resistors R15 and R20 which adjust its gain to a workable instrument gain as above-discussed. A resistor R19 is seen coupled between line 226 and ground via line 238. Line 232 is shown extending to flag 240 carrying the analog out for analyte B signal.

Figure 6:
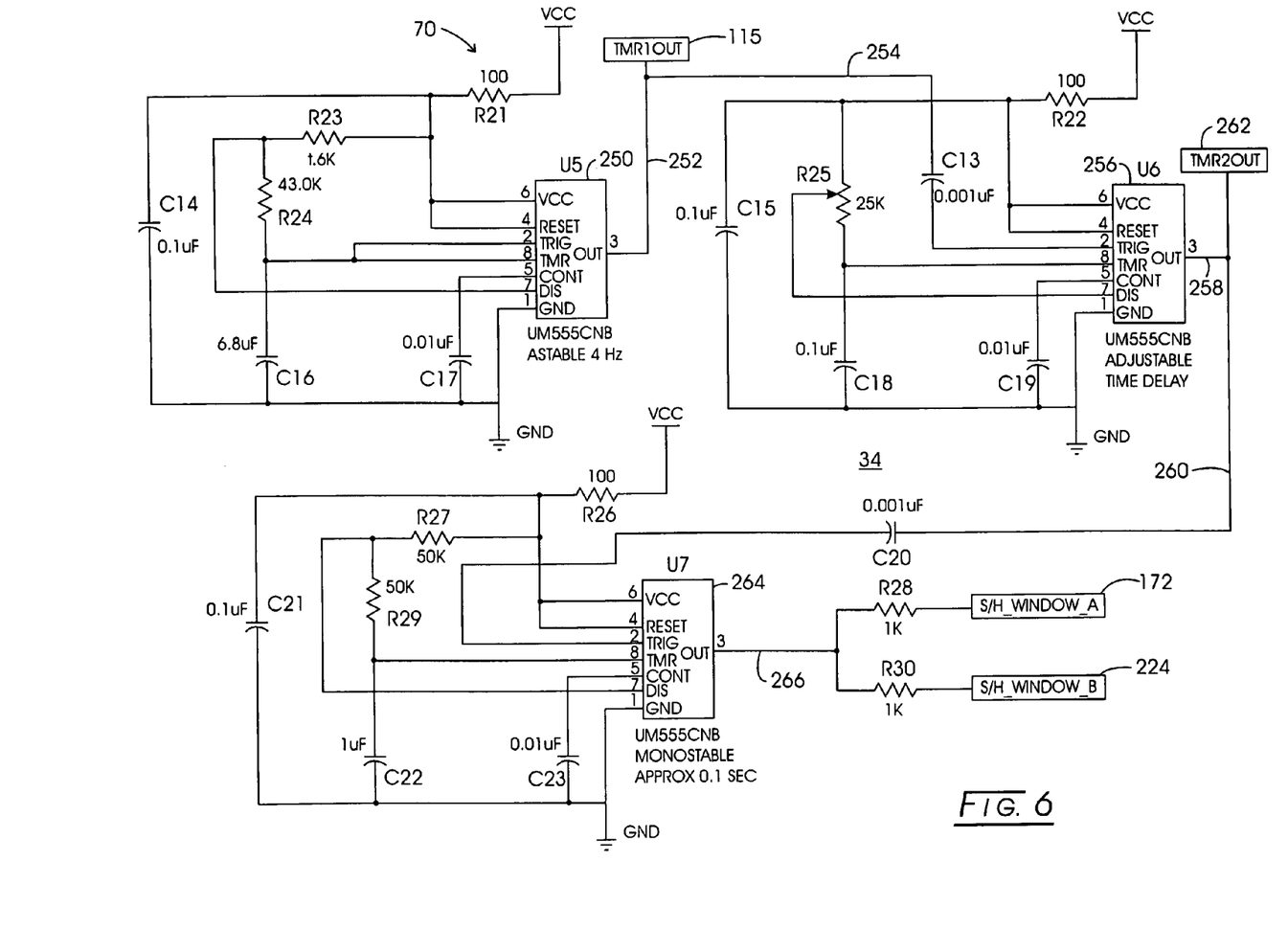
FIG. 6 is an electrical schematic diagram showing timing circuits employed with the circuitry of FIGS. 4 and 5.

FIG. 3 shows that diode D1 was energized in pulsed fashion via line 114 in consequence of the application of a timer 1 out signal represented at a flag 115. Similarly, FIGS. 4 and 5 show a sample and hold control as asserted from sample and hold window flags 172 and 224. Referring to FIG. 6, flags 115, 172 and 224 reappear in conjunction with a timing circuit. Looking to the figure, a timer 250 is seen to be configured in conjunction with capacitors C14, C16 and C17 along with resistors R21, R23 and R24 to provide an output at line 252 deriving the timer 1 output represented at flag 115 and extending to transistor Q1 for the pulse drive of light emitting diode D1.

The signal at line 252 also is directed via line 254 incorporating coupling capacitor C13 to the trigger input of an identical timer 256. Timer 256 is configured with capacitors C13, C15, C18 and C19 as well as variable resistor R25 and resistor R22 to provide an adjustable time delay at its output at line 258. Line 258 extends to line 260 which, in turn, extends from a test point 262 to the trigger input of another timer 264. While timer 250 is developed for astable operation, timer 264 is configured for monostable operation. In this regard, it is so configured utilizing capacitors C21, C22 and C23 as well as resistors R26, R27 and R29. The resultant output at line 266 is directed through resistor R28 to provide the signal for sample and hold window A as represented at flag 172 and through resistor R30 to provide the sample and hold window B signal represented at flag 224.

It should be apparent to those skilled in the art that the timing functions as described and carried out by the circuit of FIG. 6 can also be carried out by other devices such as microprocessors, programmable logic devices and the like.

Figure 7:
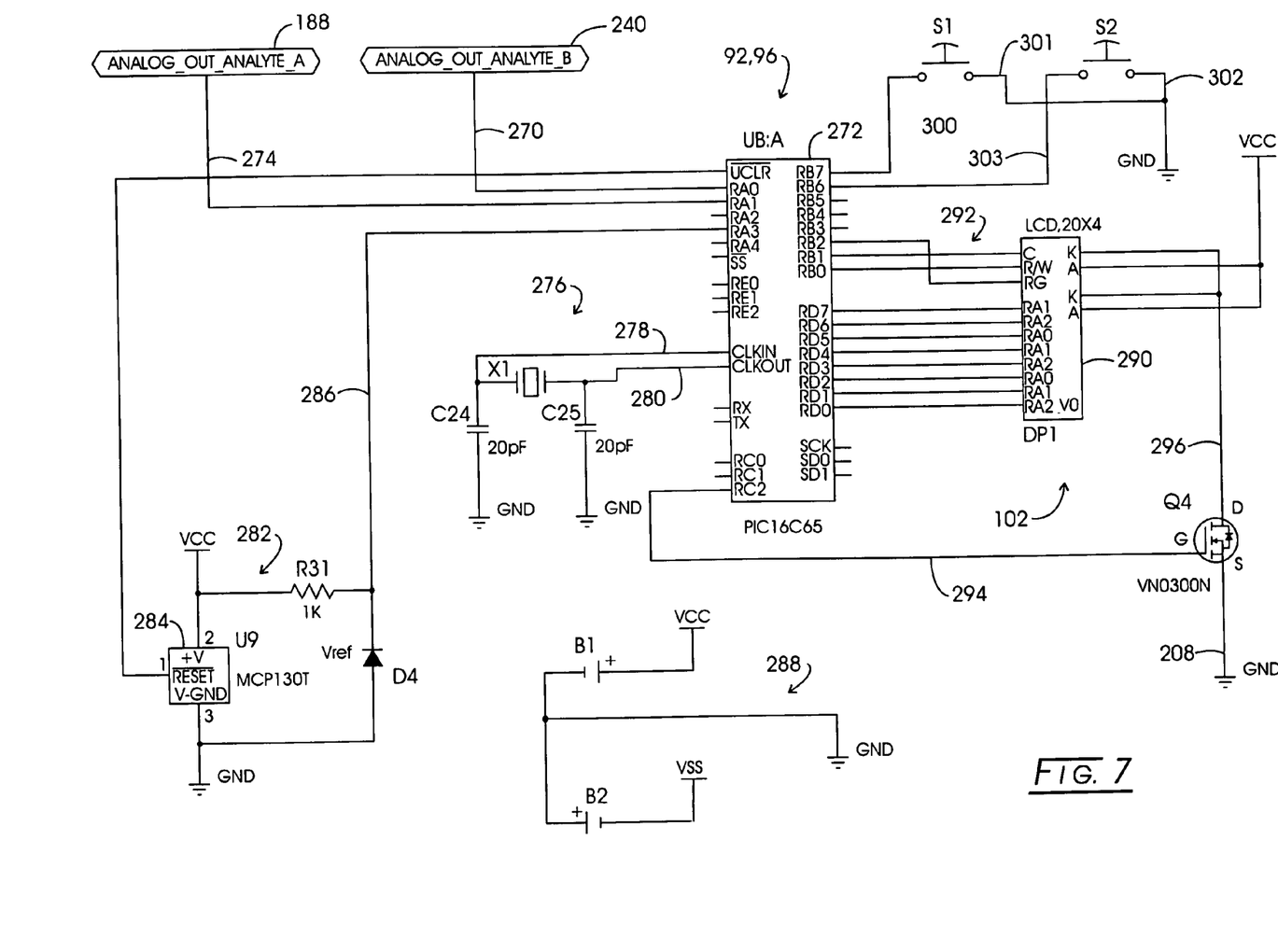
FIG. 7 is an electrical schematic diagram showing a microprocessor user interface section of the apparatus of the invention.
Figure 8:
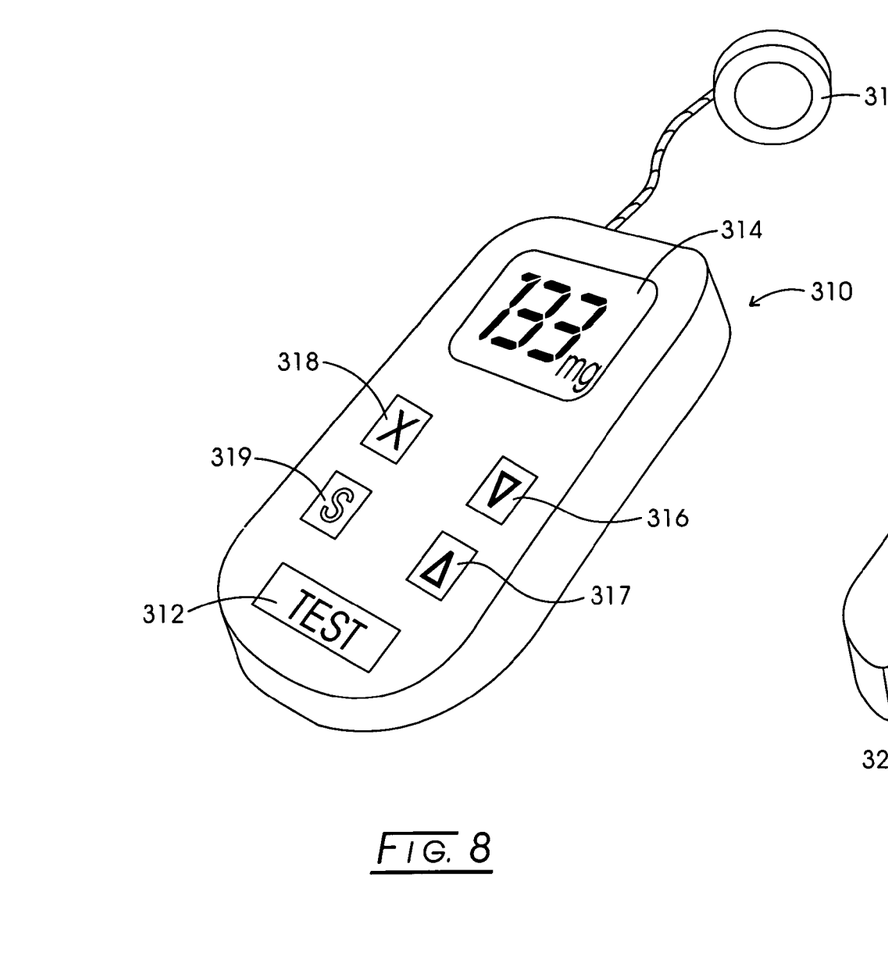
FIG. 8 is a perspective view of a housing for the circuitry of the invention.

The analog out signal for analyte A represented at flag 188 in connection with FIG. 4 and the analog out signal for analyte B represented at flag 240 in FIG. 5 are introduced to microprocessor-based circuitry. Referring to FIG. 7, those flags reappear, flag 240 directing the analog output for analyte B via line 270 to the RA0 input of a microprocessor 272. Similarly, the analog value for analyte A is directed via line 274 to the RA1 terminal of microprocessor 272. Those inputs are digitized and then treated, for instance, as discussed in connection with FIG. 2. Device 272 is configured with a clock network represented generally at 276 which is configured with crystal X1, and capacitors C24 and C25. The output of network 276 at lines 278 and 280 extend respectively to the clock-in and clock-out terminals of device 272. A reset network is represented generally at 282 incorporating reset device 284 which is configured with resistor R31 and voltage reference diode D4 to provide a voltage reference input at line 286 extending to terminal RA3 of device 272. Battery implemented supply is shown in general at network 288 as incorporating batteries B1 and B2.

Microprocessor 272 performs in conjunction with a liquid crystal display 290 by communication therewith via lead array 292. Device 290 is backlighted via signal from microprocessor 272 as shown at line 294 extending to the gate of field effect transistor Q4, the drain terminal of which at line 296 extends to the K and A terminals of display 290 and the source terminal of which extends to ground via line 298. Switches S1 and S2 are provided to carry out a general switching utility, the switches being shown configured with lines 300–303 in conjunction with device 272, terminals RB7 and RB6.

Table 1 below identifies various components described in connection with FIGS. 3–7.

FIGS. 8–15 illustrate a variety of device configurations within which the above-described circuitry may be incorporated. Looking to FIG. 8, a device represented generally at 310 is seen incorporating a remote sensor head 312. A test start switch 313, a liquid crystal display 314 and up and down switches 316, 317 which may be actuated to scroll a menu at display 314. Other potential switches are shown at 318 and 319.

Figure 9:
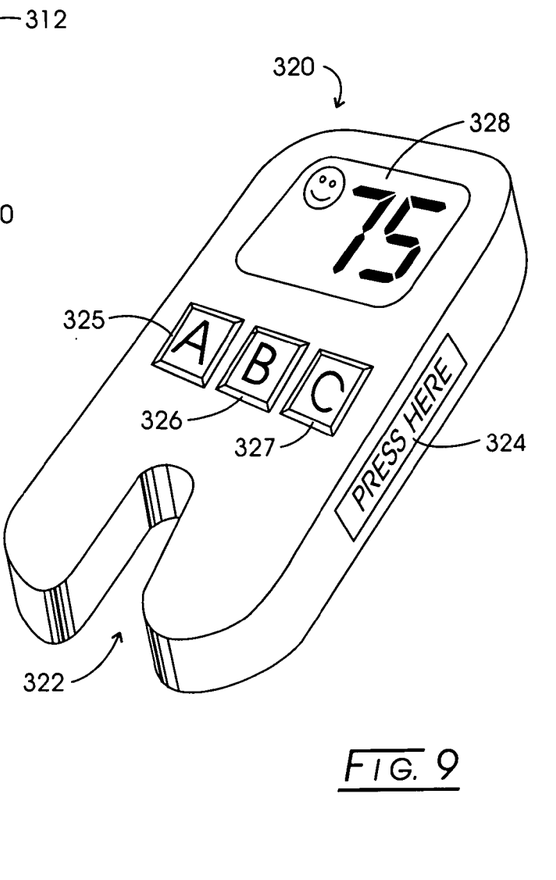
FIG. 9 is perspective view of a housing structure incorporating the circuitry of the invention.

Looking to FIG. 9, another device is represented in general at 320. Device 320 includes a slot 322 carrying the optics which may be inserted over an earlobe or the like. Test are carried out by actuating switches 324-327 and a liquid crystal display is shown at 328.

Figure 10:
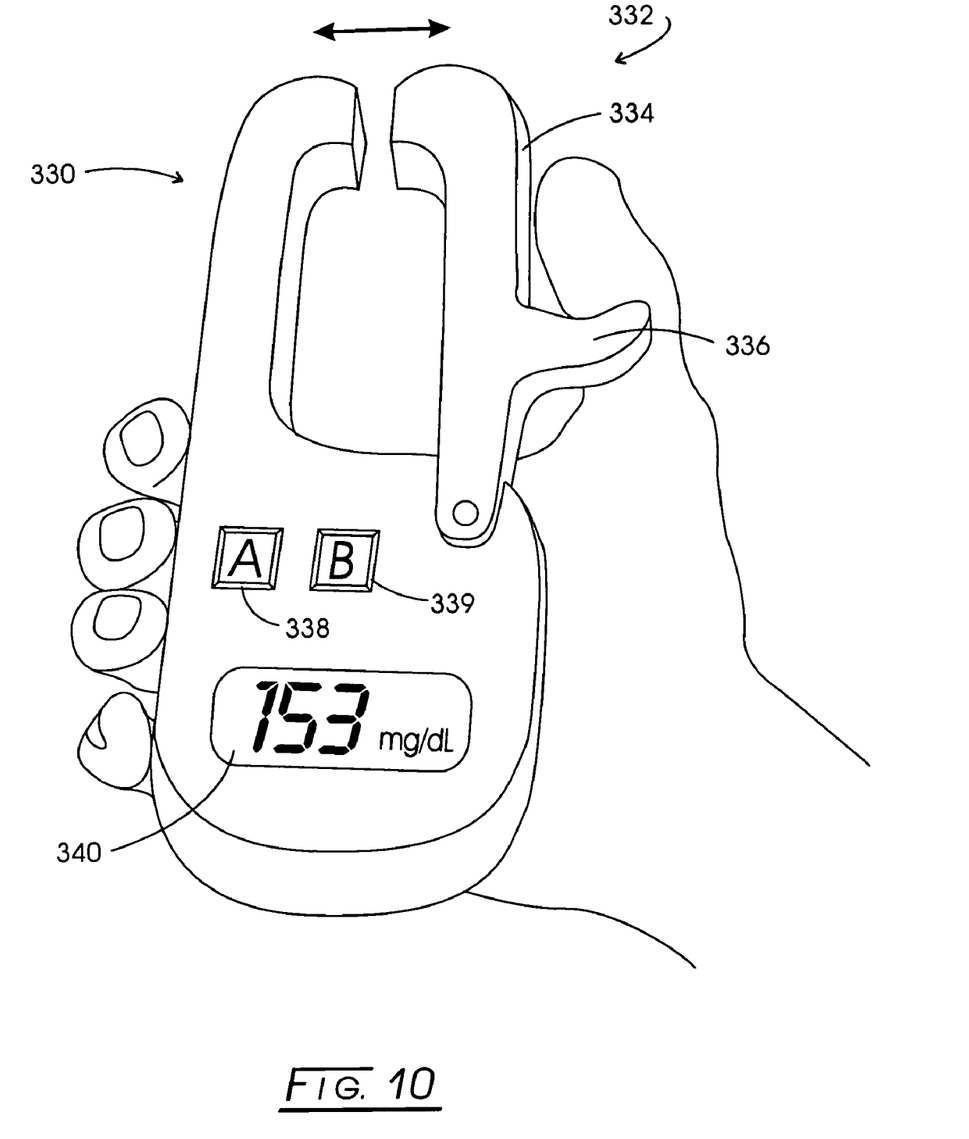
FIG. 10 is a perspective view of a housing which may incorporate the circuitry of the invention.

Referring to FIG. 10 another device structuring is represented generally at 330. Device 330 incorporates an articulated spring biased jaw represented generally at 332 which carries a sensor head. In this regard, biased jaw 334 is configured with a thumb tab 336. The device includes switches 338 and 339 as well as a liquid crystal display 340. With the arrangement, advantageous pressure can be applied against that portion of the anatomy through which analyte measurement is being made.

Figure 11:
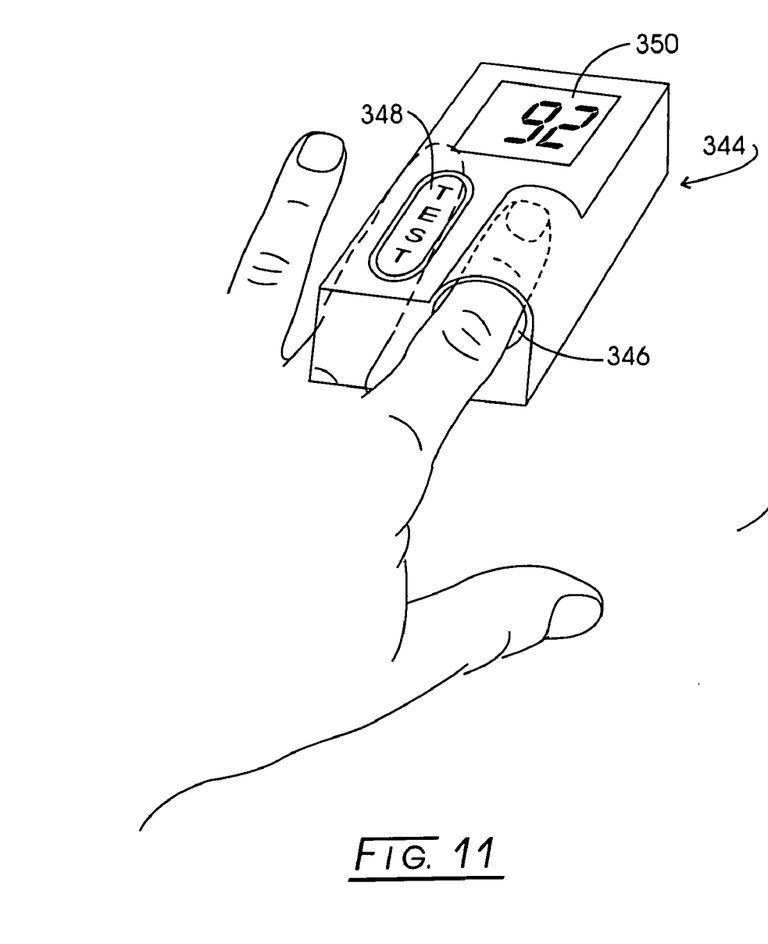
FIG. 11 is a circuit diagram of a housing which may incorporate the circuitry of the invention.

Looking to FIG. 11, a device represented generally at 344 is seen to incorporate a finger cavity 346 within which the user inserts an appropriate finger and wherein the optical analyzing components are located. A switch is represented at 348 and a liquid crystal display is shown at 350.

Figure 12:
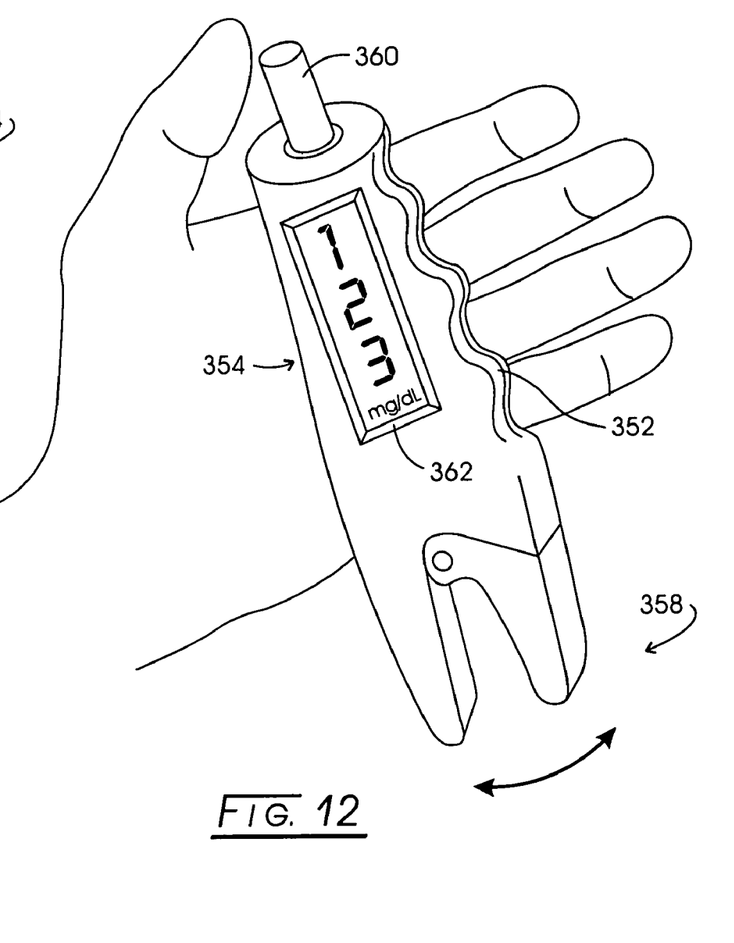
FIG. 12 is a schematic diagram of a housing which may incorporate the circuitry of the invention.
Figure 13:
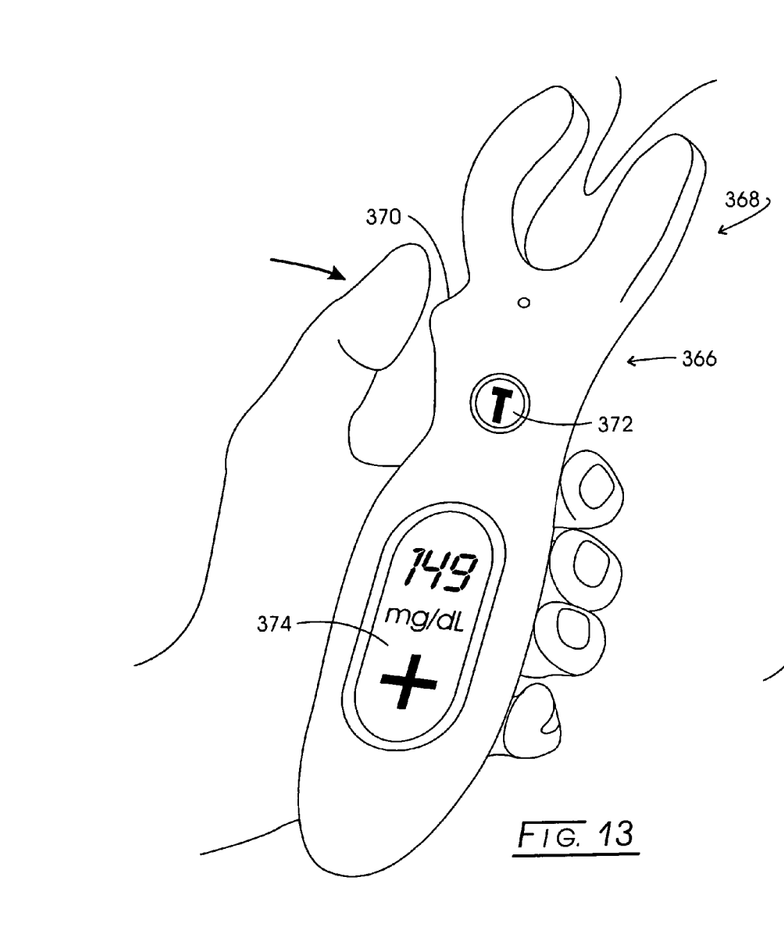
FIG. 13 is a perspective view of a housing which may incorporate the circuitry of the invention.

Looking to FIG. 12, another device is represented at 354 which is configured with a rubber grip surface with finger receiving contours and a jaw assembly represented generally at 358 which is spring biased toward a closed orientation. These jaws are opened by depressing thumb button 360. A liquid crystal display is shown at 362. Device 358 is actuated to undertake a test upon the closure of jaw assembly 358 to a certain extent, for example, ¼ inch. Referring to FIG. 13, a device is represented generally at 366 which is hand held having an articulated head with jaws represented generally at 368 which are biased into a closed position and can be actuated from a thumb tab 370. A switch is shown at 372 for taking a test reading and a liquid crystal display readout is shown at 374. Jaws 368 may be manipulated to pinch skin, for example.

Figure 14:
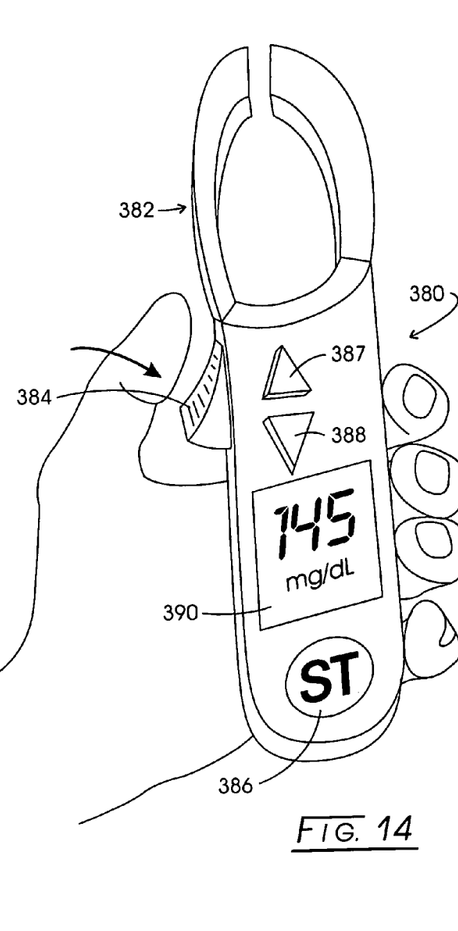
FIG. 14 is perspective view of a housing which may incorporate the circuitry of the invention.

Looking to FIG. 14, another device is represented in general at 380. Device 380 also incorporates jaws represented generally at 382 which are biased towards a closed position and may be opened by depressing thumb tab 384. The device is formed with a store switch 386, for saving a reading, for example, for trending. The device also includes up/down switches 387 and 388 which may be used to carry out a scrolling function in conjunction with liquid crystal display 390.

Figure 15:
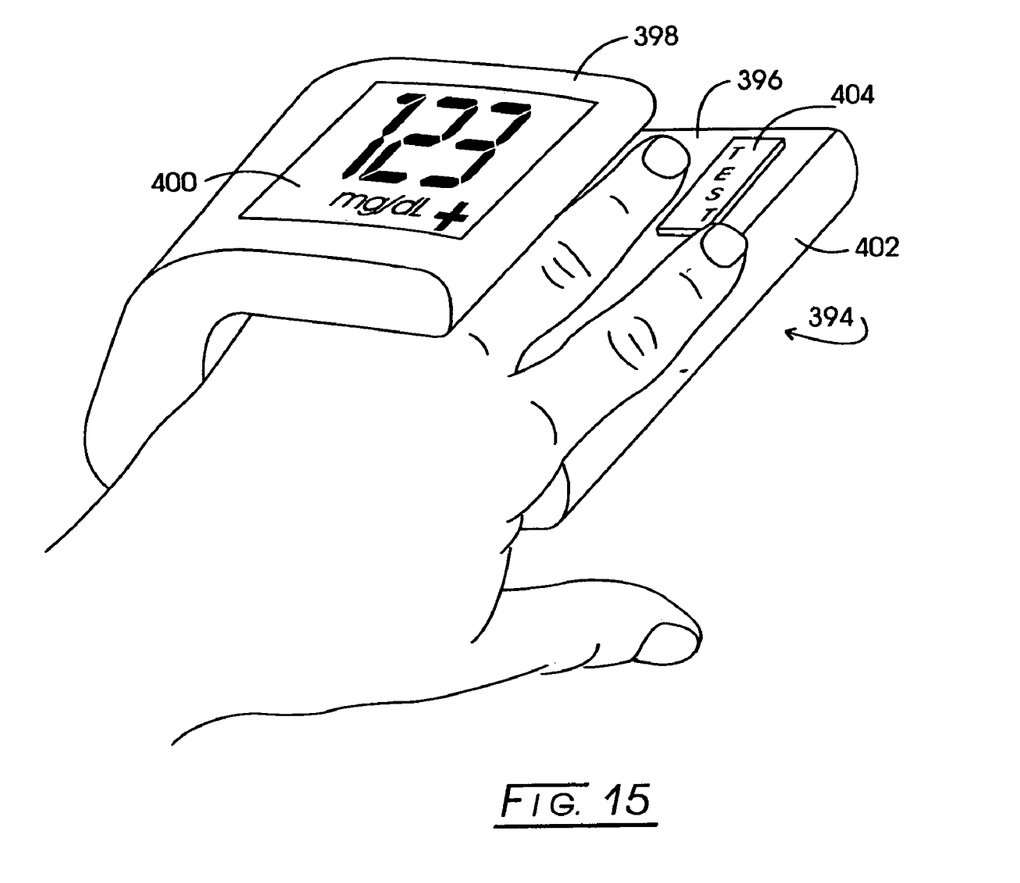
FIG. 15 is a perspective view of a housing which may incorporate the circuitry of the invention.

Referring to FIG. 15, another device is represented generally at 394. Device 394 is configured with a U-shaped chamber 396 having an upper portion 398 carrying a liquid crystal display 400 and a more outwardly extensive lower portion 402 which is structured at its outwardly disposed surface to carry a switch 404. Device 394 may, for instance, be employed to direct infrared beams through the web portions of the human hand.

Although the devices illustrated FIGS. 8–15 shown all of the components incorporated within a single housing, the invention is not limited to these embodiments. The various components may be housed with one more housings. For example, the display may be located at a site remote from the patient. It also may be convenient, for example in a hospital setting, to provide a central processor in communication with the IR source, optical detector, and display.

TABLE 1

| Count | Component | Ref/Des | Value | Description |
|---|---|---|---|---|
| 2 | Battery | B1 B2 | | Li-Ion or typi |
| 2 | CAP200-CERAMIC | C24 C25 | 20 pF | |
| 2 | CAP400A | C13 C20 | 0.001 uF | Capacitor |
| 3 | CAP400A | C17 C19 C23 | 0.01 uF | Capacitor |
| 4 | CAP400A | C14 C15 C18 C21 | 0.1 uF | Capacitor |
| 7 | CAP400A | C3 C4 C5 C8 C9 C10 C22 | 1 uF | Capacitor |
| 1 | CAP400A | C16 | 6.8 uF | Capacitor |
| 4 | CAP400A | C6 C7 C11 C12 | 10 uF | Capacitor |
| 2 | CAP400A | C1 C2 | 10 uF | Capacitor |
| 1 | CRYSTAL_ATS49 | X1 | CRYSTAL OSC | Crystal |
| 2 | DIODE | D2 D3 | 1N914 | |
| 1 | DIODE | D4 | Vref | Ref Voltage |
| 1 | LCD, 20X4 | DP1 | | LCD Display |
| 2 | PUSHBUTTONNO | S1 S2 | Momentary | Key or PB, Norm Open |
| 1 | PIC16C65 | U8 | 8-Bit | Typ Microprocessor |
| 1 | MCP130T | U9 | | Reset Control |
| 11 | RES400 | R3 R8 R9 R11 R12 R17 R18 R20 R28 R30 R31 | 1K | Resistor |
| 1 | RES400 | R23 | 1.6K | Resistor |
| 4 | RES400 | R4 R7 R13 R16 | 3.3M | Resistor |
| 1 | RES400 | R24 | 43.0K | Resistor |
| 2 | RES400 | R27 R29 | 50K | Resistor |
| 3 | RES400 | R21 R22 R26 | 100 | Resistor |
| 6 | RES400 | R5 R6 R10 R14 R15 R19 | 100K | Resistor |
| 2 | RES400 | R1 R2 | 500K | Resistor |
| 1 | TRIMPOT, SIDE | R25 | 25K | Potentiometer |
| 1 | LED | D1 | NIR | NIR LED |
| 2 | LM358 | U3 U4 | | Op-Amp |
| 3 | LM555CNB | U5 U6 U7 | | Timer |
| 4 | NMOS_TO-92_MOD | Q1 Q2 Q3 Q4 | VN0300N | NMOS FET |
| 2 | OPT-DETECTOR | U1 U2 | | |

Since certain changes may be made in the above-described system, apparatus and method without departing from the scope of the invention herein involved, it is intended that all matter contained in the above description or shown in the accompanying drawings shall be interpreted as illustrative and not in a limiting sense.

We claim:

1. A non-invasive method for measuring the concentration of an unknown blood analyte present in a patient, which comprises the steps of:
   (a) determining the concentration of a reference analyte present in said patient;
   (b) non-invasively, optically measuring the concentrations of said reference analyte and said unknown analyte;
   (c) displaying said measured unknown analyte concentration when said measured reference analyte concentration and said determined reference analyte concentration are substantially the same; and
   (d) if said measured reference analyte concentration and said determined reference analyte concentration are not substantially the same, applying an adjustment factor to said measured unknown analyte concentration and displaying said unknown analyte concentration.

2. The method of claim 1, wherein said reference analyte comprises cholesterol and said unknown analyte comprises glucose.

3. The method of claim 1, wherein said reference analyte comprises keratin and said unknown analyte comprises glucose.

4. The method of claim 1, wherein said adjustment factor of step (d) comprises a value selected from a look-up table of values based on the concentration difference between said determined reference analyte concentration and said measured reference analyte concentration.

5. The method of claim 1, wherein said step (a) comprises determining the concentration of said reference analyte in said patient by conducting an in vitro blood sample analysis.

6. The method of claim 1, wherein said steps (b), (c), and (d) are performed using an instrument comprising:
   (i) an IR source generating an IR output capable of penetrating through target tissue of said patient to produce a tissue IR output correlative with said reference analyte concentration and said unknown analyte concentration,
   (ii) an optical detector capable of detecting said tissue IR output,
   (iii) a signal treatment system for converting said tissue IR output into said reference analyte concentration and said unknown analyte concentration,
   (iv) memory capable of storing said determined reference analyte concentration, said measured reference analyte and unknown analyte concentrations, and said adjustment factor, (v) a microprocessor programmed to compare said detected reference analyte concentration to said determined reference analyte concentration and transmit said detected unknown analyte concentration to said display when said detected reference analyte concentration and said determined reference analyte concentration are substantially the same, or to apply said adjustment factor to said unknown analyte concentration and transmit said unknown analyte concentration to said display when said detected reference analyte concentration and said determined reference analyte concentration are not substantially the same, (vi) a display for displaying said unknown analyte concentration, and (vii) said IR source, said optical detector, said signal treatment system, said memory, said microprocessor, and said display being in communication.

7. The method of claim 6, wherein one or more of said IR source, optical detector, signal treatment system, memory, microprocessor, or display are housed in one or more housings.

8. The method of claim 6, wherein one or more of said signal treatment system, said memory, said microprocessor or said display are located at a site remote from said patient.

9. The method of claim 6, wherein said optical detector comprises said signal treatment system.

10. The method of claim 6, wherein said signal treatment system treats said IR source output by one or more of autozeroing, amplifying, or filtering.

11. An instrument for non-invasively measuring the concentration of an unknown blood analyte in a patient, which comprises:

(a) an IR source generating an IR output capable of penetrating through target tissue of said patient to produce a tissue IR output correlative with said reference analyte concentration and said unknown analyte concentration;

(b) an optical detectors capable of detecting said tissue IR output;

(c) a signal treatment system for converting said tissue IR output into said reference analyte concentration and said unknown analyte concentration;

(d) memory capable of storing said determined reference analyte concentration, said measured reference analyte and unknown analyte concentrations, and said adjustment factor;

(e) a microprocessor programmed to compare said detected reference analyte concentration to said determined reference analyte concentration and transmit said detected unknown analyte concentration to said display when said detected reference analyte concentration and said determined reference analyte concentration are substantially the same, or to apply said adjustment factor to said unknown analyte concentration and transmit said unknown analyte concentration to said display when said detected reference analyte concentration and said determined reference analyte concentration are not substantially the same;

(f) a display for displaying said unknown analyte concentration; and (g) said IR source, said optical detector, said signal treatment system, said memory, said microprocessor, and said display being in communication.

12. The instrument of claim 11, wherein said optical detector comprises said signal treatment system.

13. The instrument of claim 11, wherein said reference analyte comprises cholesterol and said unknown analyte comprises glucose.

14. The instrument of claim 11, wherein said reference analyte comprises keratin and said unknown analyte comprises glucose.

15. The instrument of claim 11, wherein one or more of said IR source, optical detector, signal treatment system, memory, microprocessor, or display are housed in one or more housings.

16. The instrument of claim 11, wherein one or more of said signal treatment system, said memory, said microprocessor or said display are located at a site remote from said patient.

17. The instrument of claim 11, wherein said signal treatment system treats said IR source output by one or more of autozeroing, amplifying, or filtering.

* * * * *

UNITED STATES PATENT AND TRADEMARK OFFICE
CERTIFICATE OF CORRECTION

| | | |
|---|---|---|
| PATENT NO. | : 7,039,448 B2 | Page 1 of 1 |
| APPLICATION NO. | : 10/832873 | |
| DATED | : May 2, 2006 | |
| INVENTOR(S) | : Robert P. Schlegel, John M. Ruhl and Steven V. Ricca | |

It is certified that error appears in the above-identified patent and that said Letters Patent is hereby corrected as shown below:

On the title page: please replace item [75] named inventor "John M. Rihl" with -- John M. Ruhl --.

Signed and Sealed this

Eighteenth Day of July, 2006

JON W. DUDAS
*Director of the United States Patent and Trademark Office*